United States Patent [19]

Harwin

[11] Patent Number: 5,549,691
[45] Date of Patent: Aug. 27, 1996

[54] ACETABULAR CUP

[76] Inventor: Steven F. Harwin, 1050 Park Ave., New York, N.Y. 10028

[21] Appl. No.: 191,332

[22] Filed: Feb. 3, 1994

[51] Int. Cl.⁶ .................................................. A61F 2/32
[52] U.S. Cl. .............................. 623/22; 623/11; 623/16; 623/18
[58] Field of Search ..................... 623/11, 16, 18, 623/22–23; 606/62, 65, 67, 72–73, 60, 86; 411/452–454, 456, 469

[56] References Cited

U.S. PATENT DOCUMENTS

| | | |
|---|---|---|
| 2,910,978 | 3/1955 | Urist . |
| 3,528,109 | 1/1968 | Scales . |
| 3,685,058 | 8/1972 | Tronzo . |
| 3,808,606 | 5/1974 | Tronzo . |
| 3,896,504 | 7/1975 | Fischer . |
| 3,903,549 | 9/1975 | Deyerle . |
| 4,101,985 | 7/1978 | Baumann et al. . |
| 4,840,632 | 6/1989 | Kampner . |
| 4,871,368 | 10/1989 | Wagner . |
| 5,021,062 | 6/1991 | Adrey et al. . |
| 5,163,961 | 11/1992 | Harwin . |
| 5,222,984 | 6/1993 | Forte ........................................ 623/18 |

FOREIGN PATENT DOCUMENTS 240542 10/1925 United Kingdom ................... 411/452

Primary Examiner—Randall L. Green
Assistant Examiner—P. Zuttarelli
Attorney, Agent, or Firm—Rosenman & Colin

[57] ABSTRACT

An acetabular prosthesis comprises an acetabular cup in the form of a hollow hemispherical dome having at least two blind sockets on the outer convex surface of the dome spaced apart relative to the rim of the dome, each blind socket having an entrance facing toward the top of the dome for receiving a barb and for fixedly securing the barb to the socket. The acetabular cups and barbs can be provided as sets of different sizes.

15 Claims, 2 Drawing Sheets

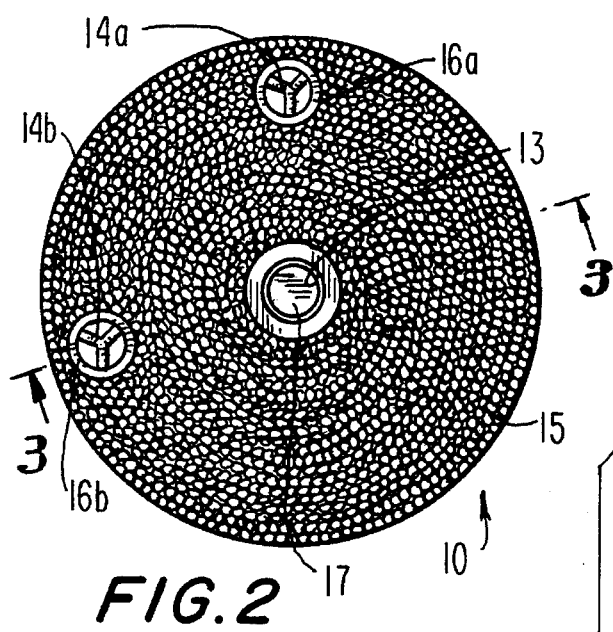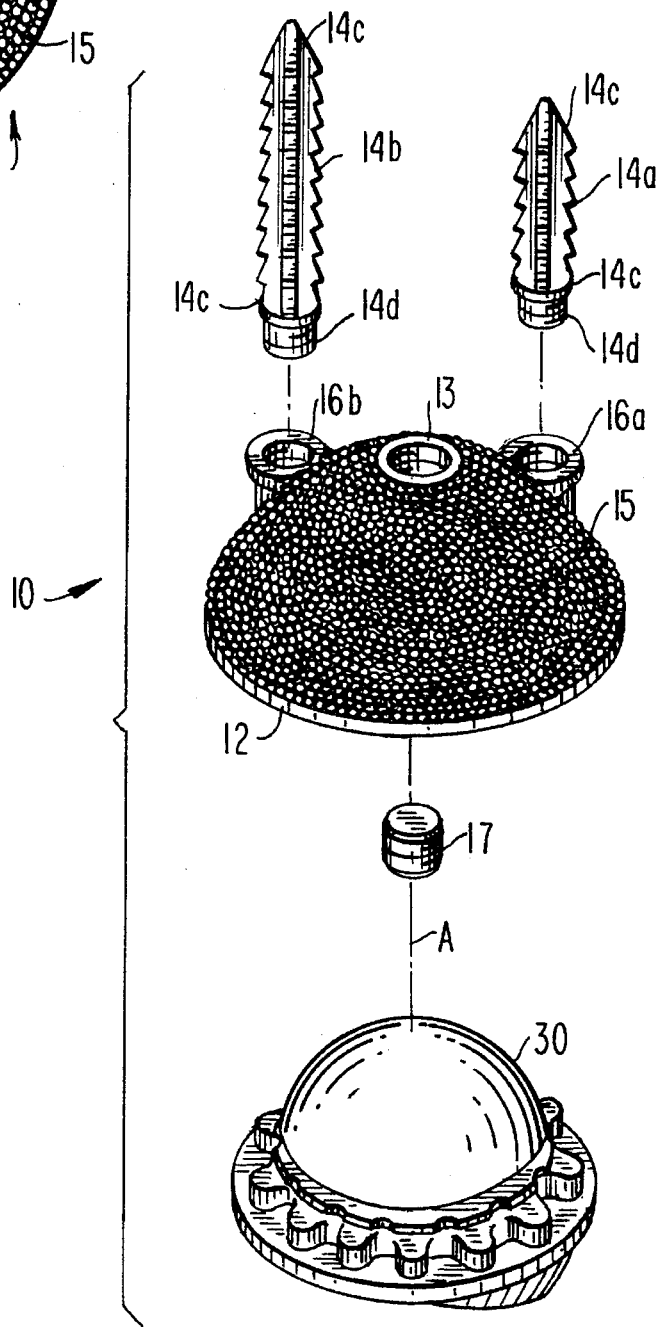

ACETABULAR CUP

FIELD OF THE INVENTION

The present invention relates to an acetabular prosthesis assembly, and more particularly to an improved acetabular prosthesis assembly including modular barbs for affixing the prosthesis to the acetabulum.

Acetabular prostheses generally comprise a low profile, hollow hemispherical metal acetabular cup that receives a plastic insert also of hollow hemispherical shape. The cup and plastic insert cooperate with a femoral stem component that has a ball at its distal end, the ball being inserted into the hollow plastic insert to complete the total hip prosthesis.

The prior art has proposed an acetabular cup assembly comprising a plurality of barbs or the like projecting from the convex outer surface of a hollow acetabular cup. The prior art has also proposed a hollow acetabular cup having a plurality of circular bores therethrough so that one or more bone screws or barbs can be inserted through the bores to affix the cup to the acetabulum.

SUMMARY OF THE INVENTION

The present invention provides an acetabular prosthesis, comprising an acetabular cup in the form of a hollow dome having a top, bottom, a convex outer surface, a concave inner surface and a rim at the bottom of the dome. At least two blind sockets are provided on the outer surface of the dome spaced apart relative to the rim, each blind socket having an entrance facing toward the top of the dome for receiving a barb and means for fixedly securing the barb to the socket.

By means of the present invention, a set of barbs of different lengths is provided with the acetabular cup so that the surgeon can select the desired length of barb to be used for each socket. The acetabular cup is implanted such that the barbs enter the superior and posterior portions of the acetabulum. Depending upon the individual patient, the barbs selected may be of the same length or of unequal lengths, thus providing the surgeon with substantial flexibility to provide the optimum implantation. The blind sockets prevent any plastic debris formed by abrasion of the plastic inner liner by the metal acetabular cup during use of the prosthesis from escaping from the cup and entering the acetabulum.

BRIEF DESCRIPTION OF THE DRAWINGS

The present invention is illustrated in terms of its preferred embodiments in the accompanying drawings, in which:

FIG. 1 is an exploded view in perspective of the acetabular cup prosthesis of the present invention;

FIG. 2 is a top plan view of the acetabular cup prosthesis in its fully assembled configuration;

DETAILED DESCRIPTION

Figure 3:
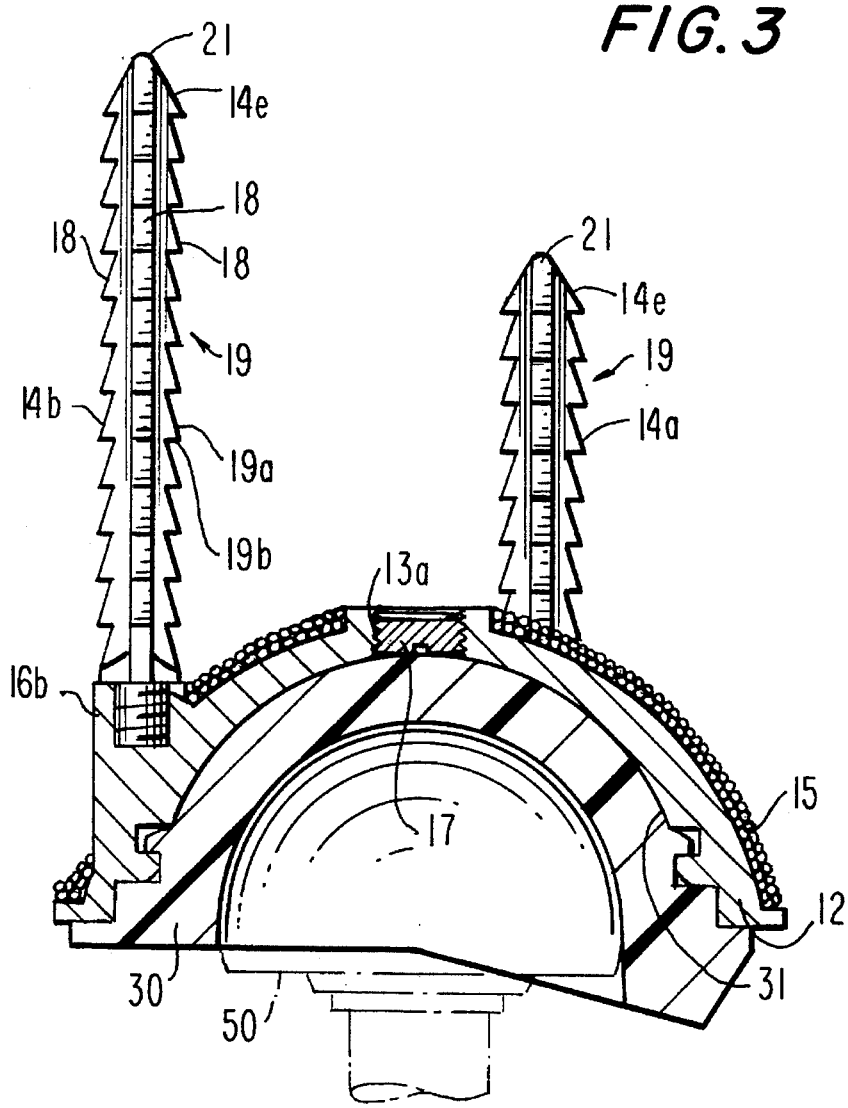
FIG. 3 is an elevational view in section taken along lines 3—3 of FIG. 2.
Figure 4:
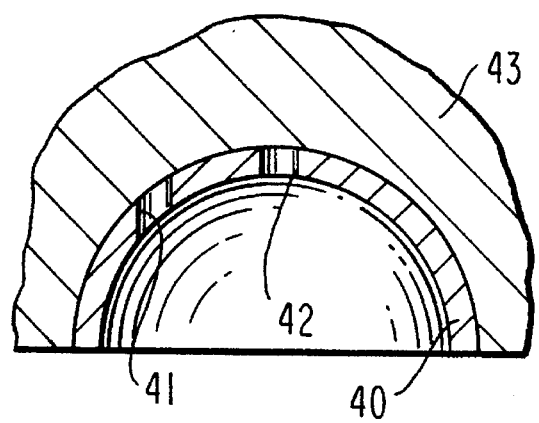
FIG. 4 is an elevational view in section schematically depicting the use of a template to locate the acetabular cup prosthesis of the invention before insertion into the acetabulum.

FIG. 1 shows the acetabular cup prosthesis assembly 10 comprising a low profile, hemispherical metal acetabular cup 12 in the form of a hollow dome having two modular barbs 14a, 14b affixed thereto by threaded engagement into blind sockets 16a, 16b, respectively, projecting from the outer surface of cup 12. Central aperture 13 is provided at the apex or top of cup 12 so that the dome of the acetabulum can be viewed during installation of cup 12, as will be described hereinafter. Preferably, the convex outer surface of cup 12 carries a bone-ingrowth porous coating 15. After insertion of cup 12 into the acetabulum, plug 17 will close aperture 13 and a polyethylene or other suitable plastic liner 30 will be inserted into cup 12, as is usual. See FIG. 3.

In the preferred embodiment shown in FIGS. 1–4, cup 12 has two cylindrical blind sockets 16a, 16b located at 12:00 and 8:30, respectively as viewed in FIG. 2. The cup 12 in the position shown in FIG. 2 is for implantation into the right-hand acetabulum. For implantation into the left-hand acetabulum, the cup 12 is rotated 105° so that sockets 16b, 16a will be at 12:00 and 3:30, respectively. Barbs 14a, 14b are thus implanted into the superior and posterior portions of the acetabulum of the right- and left-hand coaxal bones, respectively.

Barbs 14a, 14b will enable cup 12 to be rigidly affixed to the hip bone, prevent rotation of cup 12 about its axis of rotation A (FIG. 1) and prevent tilting or "pull-out" of cup 12 after implantation.

It is an important feature of the present invention that the proximal end 14c of each barb 14a, 14b is fixedly secured to sockets 16a, 16b, such as by threaded engagement of threads 14d with threads 16c tapped into each socket 16a, 16b. Any plastic debris formed by abrasion of the plastic inner liner 30 by the metal cup 12 is therefore prevented from escaping from cup 12 and entering the acetabulum. In previous devices using screws to affix the acetabular cup, such debris could exit the cup through the screw holes in the cup and possibly cause osteolysis.

As best seen in FIG. 2, barbs 14a, 14b have three ribs 18 spaced apart by 120°, each provided with several teeth 19 having an outer edge 19a extending proximally and radially outward from the longitudinal axis of barb 14 and an outer edge 19b that is preferably perpendicular to the longitudinal axis. Each barb 14 terminates at its distal end 14e in a blunt point 21. In this manner, the barbs 14 will readily penetrate the cancellous bone of the pelvis and will resist being withdrawn. While edge 19b is preferably perpendicular to the longitudinal axis of the barb 14, it may also extend distally and radially inwardly (not shown).

Before assembly 10 is actually implanted, the surgeon will have previously determined from x-rays the diameter of cup 12 and the length of barbs 14a, 14b expected to be used, and he will then order and receive a set of cups 12, their mating inserts 30 and barbs 14a, 14b spanning a range of sizes bracketing the selected diameter of cup 12 and length of barbs 14a, 14b. After the acetabulum is exposed, the surgeon will make the final selection of cups and barbs. The cups, inserts and barbs are preferably delivered to the surgeon in separate sterile packages, one unit per package. If desired, the cups 12 can be delivered with caps (not shown) closing sockets 16a, 16b or with the smallest size barb installed.

During the surgical procedure, template 40 (FIG. 4) will be used to locate the desired position for cup 12. Template 40 has three through bores corresponding in location to sockets 16a, 16b and aperture 13. Two such bores are visible in FIG. 4, namely bores 41 and 42 corresponding to socket 16b and aperture 13, respectively. Using a drill whose diameter is smaller than the diameter of a circle enclosing teeth 19 of barbs 14a, 14b, the surgeon will drill pilot bores into the acetabulum 43 using the bores corresponding in location to sockets 16a, 16b. In some cases, only one barb may be used and only one pilot bore will be drilled. A stop may be used on the drill to limit the length of the pilot bore.

After the pilot bores have been drilled, the template 40 is replaced with cup 12, into which has been securely threaded barbs 14a, 14b. The barbs are then driven into the pilot bores by hammering on the rim of cup 12. The surgeon can monitor the travel of barbs 14a, 14b into the acetabulum through aperture 13. When cup 12 is flush against the acetabulum, the cup is in its final position and plug 17 is then installed. Threads 13a (FIG. 3) are tapped into cup 12 so that they become closer together at the distal end of aperture 13, whereby the final position of plug 17 preferably does not extend beyond the inner and outer surfaces of cup 12. Plug 17 thus cooperates with the blind sockets 16a, 16b to prevent escape of debris from the interior of cup 12.

Lastly, insert 30 is snapped into place within cup 12. Any conventional insert 30 and complementary recess 31 (FIG. 3) may be used, such as the scalloped-edge insert 30 depicted. Assembly 10 is then joined to the ball 50 of the femoral insert of the hip prosthesis.

In some cases, the surgeon may choose to insert cup 12 without any barbs; the sockets 16a, 16b will then provide an anti-rotational effect, since they project beyond the outer surface of cup 12 and hence enter the acetabulum. In other cases, more than two sockets can be carried by the cup (not shown), so that more than two barbs can be used.

It is presently contemplated that cup 12 will be offered in a range of sizes from 46 to 74 mm diameter in 2 mm increments, while barbs 14a, 14b will be offered in a range of lengths from 25 to 42.5 mm, in 2.5 mm increments. Other ranges of sizes may be used as well. Sockets 16a, 16b may have a bore about 0.187 inch deep and about 0.25 inches inner diameter. The sockets 16a, 16b may extend about 0.600 inches from the rim of cup 12. Aperture 13 may also be about 0.25 inches in diameter, with plug 17 sized accordingly. Other dimensions may also be used, if desired.

The materials selected for the cup 12, barbs 14a, 14b, bone-ingrowth coating 15, plug 17 and insert 30 may all be conventional. For example, the cup, bone-ingrowth coating, barbs and plug may be made of a Vitallium alloy, while the insert 30 may be made of ultrahigh molecular weight polyethylene.

It is noted that the sockets 16a, 16b are preferably not coated with the bone-ingrowth material, but, if desired, they may be so coated.

I claim:

1. An acetabular prosthesis, comprising an acetabular cup in the form of a hollow dome having a hemispherical top, a bottom, a convex outer surface, a concave inner surface, a circular rim at the bottom of the dome and at least two blind sockets on said outer surface circumferentially spaced apart relative to said rim, each blind socket having an entrance facing away from said rim and in a direction parallel to the direction the entrance of each of the other sockets is facing for receiving a barb and means for fixedly securing a barb to said socket.

2. Apparatus according to claim 1, wherein at least one of said sockets includes an elongated barb having a proximal end thereof fixedly secured to said socket by said securing means and a free distal end thereof projecting forward the top of the dome.

3. Apparatus according to claim 2, wherein the proximal end of each said barb has means cooperating with said securing means for fixedly securing said barb to said socket.

4. Apparatus according to claim 2, wherein at least two of said sockets have fixedly secured thereto barbs of unequal length.

5. Apparatus according to claim 2, wherein at least two of said sockets have fixedly secured thereto barbs of the same length.

6. Apparatus according to claim 2, wherein each of said barbs comprises three spaced apart ribs extending longitudinally from said distal end toward said proximal end, each said rib having a plurality of teeth arranged to allow said barb to be inserted into bony tissue and to resist withdrawal of said barb once inserted into bony tissue.

7. Apparatus according to claim 6, wherein each of said teeth has a first surface extending proximally and radially outward and a second surface extending distally and radially inward.

8. Apparatus according to claim 6, wherein each of said teeth has a first surface extending proximally and radially outward and a second surface extending distally and substantially perpendicular to the longitudinal axis of said barb.

9. Apparatus according to claim 1, wherein the top of the dome has a bore therethrough, and an elongated plug with opposed ends is provided for closing said bore, said plug having a preselected length such that the ends of the plug do not extend beyond said inner or outer surfaces when fully inserted in said bore.

10. An acetabular prosthesis, comprising (a) a set of elongated barbs, at least some of said barbs being of unequal length and at least some of said barbs being of the same length or; and (b) a set of hemisperical hollow dome, each having a hemispherical top, and a bottom, a convex outer surface, a concave inner surface, and a circular rim at the bottom of the dome and at least two blind sockets on said outer surface circumferentially spaced apart relative to said rim, each blind socket having an entrance facing away from said rim and in a direction parallel to the direction the entrance of each of the other sochets is facing for receiving a barb and means for fixedly securing a barb to said socket, at least some of said domes being of unequal sizes.

11. Apparatus according to claim 10, wherein the proximal end of each said barb has means cooperating with said securing means for fixedly securing said barb to said socket.

12. Apparatus according to claim 10, wherein each of said barbs comprises three spaced apart ribs extending longitudinally from said distal end toward said proximal end, each said rib having a plurality of teeth arranged to allow said barb to be inserted bony tissue and to resist withdrawal of said barb once inserted in bony tissue.

13. Apparatus according to claim 10, wherein each of said teeth has a first surface extending proximally and radially outward and a second surface extending distally and radially inward.

14. Apparatus according to claim 10, wherein each of said teeth has a first surface extending proximally and radially outward and a second surface extending distally and substantially perpendicular to the longitudinal axis of said barb.

15. Apparatus according to claim 10, wherein each of said domes has a bore therethrough, and an elongated plug with opposed ends is provided for closing said bore, said plug having a preselected length such that the ends of the plug do not extend beyond said inner or outer surfaces when fully inserted in said bore.

* * * * *